(12) United States Patent
Garza

(10) Patent No.: US 6,622,325 B1
(45) Date of Patent: Sep. 23, 2003

(54) FACIAL FATIGUE REDUCING PILLOW CONSTRUCTION

(76) Inventor: Jesse Garza, 8523 Jamestown Dr., Austin, TX (US) 78758

( * ) Notice: Subject to any disclaimer, the term of this patent is extended or adjusted under 35 U.S.C. 154(b) by 0 days.

(21) Appl. No.: 10/086,467

(22) Filed: Mar. 1, 2002

(51) Int. Cl.$^7$ ................................................. A47G 9/00
(52) U.S. Cl. ................................... 5/636; 5/639; 5/645
(58) Field of Search .......................... 5/636, 638, 639, 5/640, 644, 645

(56) References Cited

U.S. PATENT DOCUMENTS

| | | | | |
|---|---|---|---|---|
| 2,295,906 A | * | 9/1942 | Lacour | 5/636 |
| D174,778 S | * | 5/1955 | Smith | D6/601 |
| 2,835,905 A | * | 5/1958 | Tomasson | 5/636 X |
| 2,944,266 A | * | 7/1960 | Wertheimer | 5/645 |
| 3,443,267 A | * | 5/1969 | Schuckman | 5/645 |
| 3,667,074 A | * | 6/1972 | Emery | 5/636 |
| 4,074,376 A | * | 2/1978 | Bond | 5/632 |
| 4,118,813 A | * | 10/1978 | Armstrong | 5/638 |
| 4,349,925 A | * | 9/1982 | Macomber | 5/636 X |
| 4,550,458 A | * | 11/1985 | Fiore | 5/640 X |
| 4,783,866 A | * | 11/1988 | Simmons et al. | 5/639 |
| 4,858,259 A | * | 8/1989 | Simmons et al. | 5/644 |
| 4,887,326 A | * | 12/1989 | O'Brien et al. | 607/109 |
| D308,787 S | * | 6/1990 | Youngblood | 5/636 X |
| 5,018,231 A | * | 5/1991 | Wang | 5/636 |
| D318,203 S | * | 7/1991 | Zaghini | 5/636 X |
| 5,163,194 A | * | 11/1992 | Dixon | 5/636 |
| 5,163,195 A | | 11/1992 | Hill | 5/637 |
| D381,233 S | * | 7/1997 | Torbik | D6/601 |
| D388,648 S | * | 1/1998 | Bates | D6/601 |
| 5,708,998 A | * | 1/1998 | Torbik | 5/636 |
| 5,778,470 A | * | 7/1998 | Haider | 5/645 |
| 5,781,947 A | * | 7/1998 | Sramek | 5/636 |
| 5,813,065 A | | 9/1998 | Tinhorn | 5/639 |
| 5,848,448 A | * | 12/1998 | Boyd | 5/636 |
| 5,916,088 A | * | 6/1999 | Gueli | 5/639 |
| 5,926,880 A | * | 7/1999 | Sramek | 5/636 |
| 5,933,890 A | | 8/1999 | Codd | 5/636 |
| D416,742 S | * | 11/1999 | Sramek | D6/601 |
| 6,006,380 A | * | 12/1999 | Sramek | 5/636 |
| 6,026,330 A | * | 2/2000 | Chuang | 5/636 X |
| 6,052,850 A | | 4/2000 | Salido et al. | 5/644 |
| 6,427,272 B1 | * | 8/2002 | Yacoub | 5/638 |

FOREIGN PATENT DOCUMENTS

AU 36813 A * 1/1970 ................. 5/636

* cited by examiner

*Primary Examiner*—Robert G. Santos
(74) *Attorney, Agent, or Firm*—Sturm & Fix LLP

(57) ABSTRACT

A facial fatigue reducing pillow construction (10) for eliminating the application of compressive forces against the side of a user's face including the eye socket and cheek bone areas while the user's head rests on the pillow construction (10) which includes a pillow member (20) having an upper portion (22) provided with a pair of facial relief units 12 12' and a head relief unit (13) aligned along the longitudinal axis of the pillow member (20) wherein the facial relief units (12 12') create voids in the upper portion (22) of the pillow member (20) adjacent a person's eye sockets and cheek bones and the head relief unit (13) is dimensioned to receive and support the side of a user's head.

4 Claims, 1 Drawing Sheet

FACIAL FATIGUE REDUCING PILLOW CONSTRUCTION

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to the field of specially contoured sleep aids in general and in particular to a specially contoured pillow construction that eliminates the compression of the user's cheekbones and eye socket area while they are sleeping.

2. Description of Related Art

As can be seen by reference to the following U.S. Pat. Nos. 5,813,065; 5,933,890; 5,163,195; and, 6,052,850, the prior art is replete with myriad and diverse specially contoured pillow constructions designed to accommodate a broad range of individual needs.

While all of the aforementioned prior art constructions are more than adequate for the basic purpose and function for which they have been specifically designed, they are uniformly deficient with respect to their failure to provide a simple, efficient, and practical contoured pillow construction that will eliminate baggy or puffy eyes and cheek creases, which while only physically lasting for a short duration each morning, ultimately takes their toll on a person's appearance primarily due to the loss of elasticity of the compressed areas of a person's face that nightly comes into contact with the surface of a conventional pillow.

As a consequence of the foregoing situation, there has existed a longstanding need among appearance conscious individuals for a new and improved specially contoured pillow construction that is specifically designed to eliminate the compressive contact between a pillow and the user's eye socket and cheekbone area; and the provision of such a construction is a stated objective of the present invention.

BRIEF SUMMARY OF THE INVENTION

Briefly stated, the facial fatigue reducing pillow construction that forms the basis of the present invention comprises in general a cushioned pillow unit provided with a pair of face relief units and a central head relief unit disposed intermediate the face relief units.

As will be explained in greater detail further on in the specification, the pair of face relief units are formed on opposite sides of the cushioned pillow unit; wherein, each of the face relief units is optionally provided with a removable gel-filled eye relief cup element that may be prechilled prior to use to further reduce any localized swelling of the user's face in the vicinity of the face relief units.

In addition, the central head relief unit is designed and dimensioned to receive either side of the user's head to position their eye socket and cheekbone over one or the other of the face relief units while also providing ample raised support for the user's neck; and, the face and head relief units are further aligned in mirror fashion relative to the longitudinal axis of the cushioned pillow unit such that the cushioned pillow unit can be rotated 180° in the horizontal plane and the relative positioning and dimensions of the relief units will remain virtually identical.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein.

DETAILED DESCRIPTION OF THE INVENTION

Figure 2:
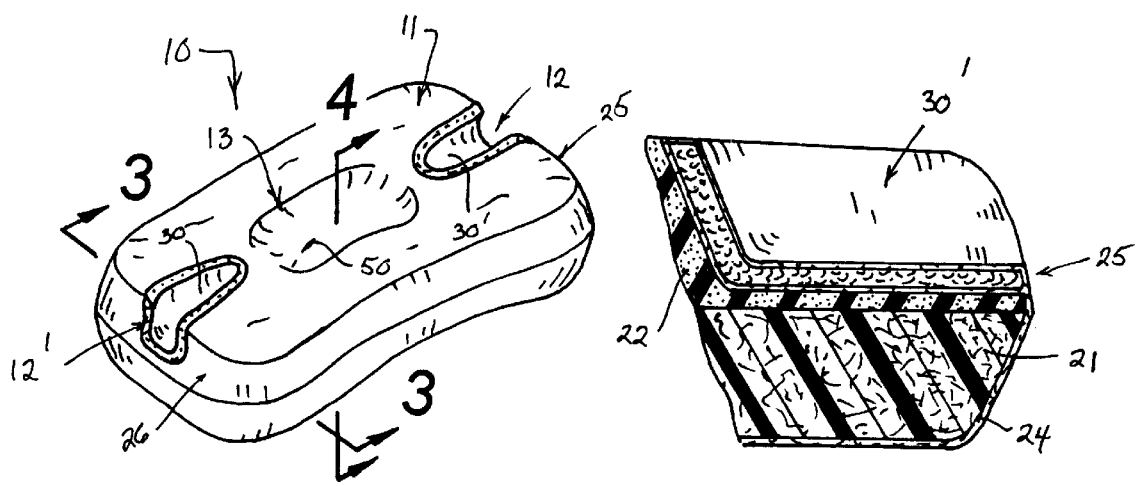
FIG. 2 is an isolated perspective view of the pillow construction.

As can be seen by reference to the drawings, and in particularly to FIG. 2, the facial fatigue reducing pillow construction that forms the basis of the present invention is designated generally by the reference number 10. The construction 10 comprises in general a cushioned pillow unit 11, a pair of face relief units 12 12' and a head relief unit 13. These units will now be described in seriatim fashion.

As can best be seen by reference to FIGS. 2 through 4, the cushioned pillow unit 11 comprises a generally rectangular pillow member 20 having a lower batting-filled portion 21 and an upper foam filled portion 22; wherein, the lower portion 21 is designed to enhance the resiliency of the composite pillow member 20 and the upper portion 22 is designed to provide structural rigidity and support to the relief units 12 12' and 13 as will be explained presently.

In addition, in the preferred embodiments of this invention illustrated in the drawings, the resilient but firm upper portion 22 of the pillow member 20 is fabricated from a block of resilient foamed material 23 such as open or closed cell foam, depending upon the degree of firmness desired in the finished pillow member 20; and, the composite pillow member 20 is further provided with a filled fabric cover 24.

Figure 5:
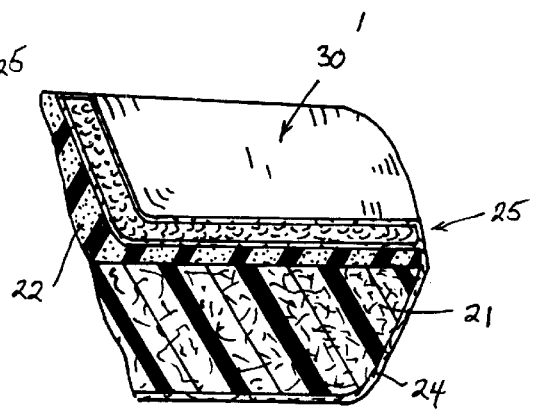
FIG. 5 is a cross-sectional view taken through line 5—5 of FIG. 3.
Figure 3:
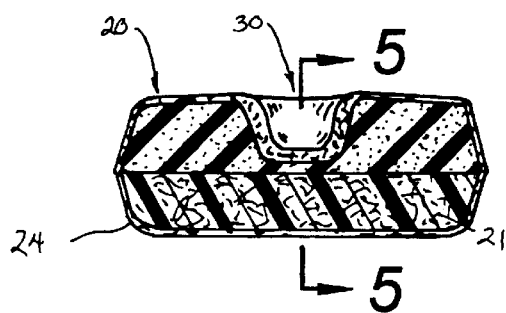
FIG. 3 is an isolated cross-sectional view taken through one of the face relief units.

Turning now to FIGS. 2, 3, and 5, it can be seen that each of the facial relief units 12 12' essentially comprise a truncated oblong recess 30 30' formed in the top surface of the pillow member 20; wherein, each recess 30 30' is aligned with the longitudinal axis of the pillow member 20 substantially penetrating the firm upper portion 22 thereof and extending outwardly through one of the opposed sides 25 26 of the pillow member 20.

As can best be appreciated by reference to FIG. 5, this invention also contemplates the provision of removable gel pack inserts 40 40' contoured to conform to the interior surfaces of the truncated oblong recesses 30 30' that comprise the facial relief units 12 12' of the pillow construction 10. These gel pack inserts 40 40' may then be either pre-chilled or pre-warmed in a well recognized fashion to provide additional therapeutic benefits for the user.

At this juncture, it should also be noted that the truncated oblong recesses 30 30' extend outwardly through the opposed sides 25 26 of the pillow member 20 so that fresh air will circulate beneath the unsupported eye socket and cheekbone area of the user as they sleep on one side or the other.

Returning once more to FIGS. 2 and 4, it can be seen that the head relief unit 13 comprises a generally shallow enlarged central recess 50 that is dimensioned to receive and partially immobilize either the right or left side of the user's head, to position one pair of the user's eye sockets and cheekbones over the appropriate facial relief unit 12 or 12'.

Figure 1:
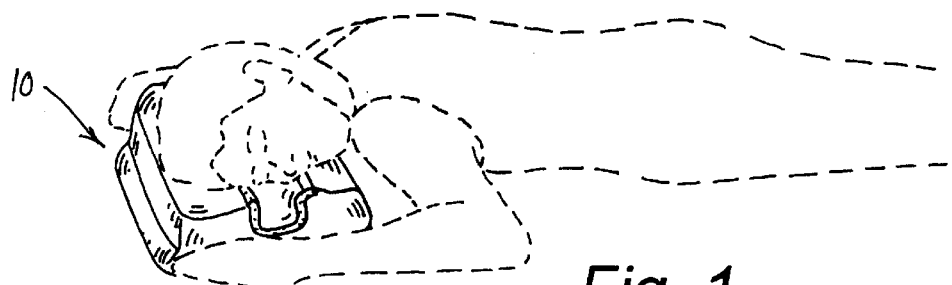
FIG. 1 is a perspective view of the facial fatigue reducing pillow construction that forms the basis of this invention in use.
Figure 4:
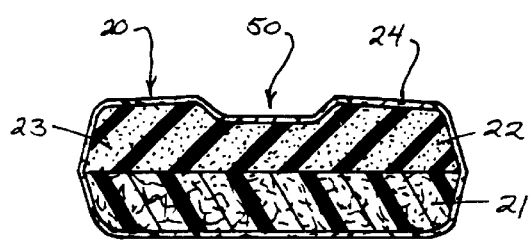
FIG. 4 is a cross-sectional view taken through line 4—4 of FIG. 3.

Furthermore, as can be seen by reference to FIGS. 3 and 4, the depth of the central recess 50 is less than one half the depth of the truncated oblong recesses 30 30' due to the fact that the transverse portions 28 29 of the pillow member 20 adjacent the central recess 50 are intended to provide support for the user's neck as depicted in FIG. 1.

By now it should be appreciated that the facial fatigue reducing pillow construction 10 that forms the basis of the present invention fulfills all of the stated objectives by virtually eliminating compressive forces being exerted in the area of the user's eye socket and cheekbone while the side of their head rests on a pillow when they are sleeping, thereby avoiding puffy eyes and crows feet at the corner of eh eye caused by compression of the skin covering the cheek bone area of a person's face.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

Having thereby described the subject matter of the present invention, it should be apparent that many substitutions, modifications, and variations of the invention are possible in light of the above teachings. It is therefore to be understood that the invention as taught and described herein is only to be limited to the extent of the breadth and scope of the appended claims.

I claim:

1. A facial fatigue pillow construction for eliminating compressive forces against a person's cheek bone and eye socket area while their head rests on the pillow construction which comprises:

a pillow unit including a generally rectangular pillow member having a longitudinal upper portion and a lower portion filled with batting material and encased in a fabric cover; and, a pair of facial relief units formed in the upper portion of the pillow member wherein each facial relief unit comprises a truncated oblong recess aligned along the longitudinal axis of the pillow member; wherein, each of the truncated oblong recesses substantially penetrates the upper portion of the pillow member, and extends through one side of the upper portion of the pillow member; and further including a pair of gel pack inserts adapted to be releasably received in said pair of facial relief units wherein, each of the gel pack inserts is dimensioned to closely conform to the walls of the truncated oblong recesses.

2. The construction as in claim 1 further comprising:

a head relief unit disposed intermediate the pair of facial relief units and including a generally shallow enlarged central recess formed in the upper portions of the pillow member and bisected by the longitudinal axis of the pillow member.

3. The construction as in claim 2; wherein, the depth of the central recess is less than one-half the depth of the truncated oblong recesses that form the facial relief units.

4. The construction as in claim 1; wherein, at least the upper portion of the pillow member comprises a block of resilient foamed material.

\* \* \* \* \*